United States Patent
Gual Pasalodos

(10) Patent No.: US 9,375,760 B2
(45) Date of Patent: Jun. 28, 2016

(54) MACHINE FOR THE INSPECTION AND DETECTION OF DEFECTS IN FRUIT PRODUCTS, AND ASSOCIATED METHODS

(71) Applicant: CITRODIAGNOSIS SELECTIVA, S.L., Albuixech (Valencia) (ES)

(72) Inventor: Mariano Gual Pasalodos, Valencia (ES)

(73) Assignee: CITRODIAGNOSIS SELECTIVA, S.L., Albuixech, Valencia (ES)

( * ) Notice: Subject to any disclaimer, the term of this patent is extended or adjusted under 35 U.S.C. 154(b) by 0 days.

(21) Appl. No.: 14/441,608

(22) PCT Filed: Nov. 14, 2013

(86) PCT No.: PCT/ES2013/070798
§ 371 (c)(1),
(2) Date: May 8, 2015

(87) PCT Pub. No.: WO2014/076346
PCT Pub. Date: May 22, 2014

(65) Prior Publication Data
US 2015/0283585 A1 Oct. 8, 2015

(30) Foreign Application Priority Data
Nov. 16, 2012 (ES) .................................. 201201171

(51) Int. Cl.
*G01N 21/00* (2006.01)
*B07C 5/36* (2006.01)
(Continued)

(52) U.S. Cl.
CPC . *B07C 5/362* (2013.01); *B07C 5/34* (2013.01); *B07C 5/342* (2013.01); *B07C 5/3422* (2013.01);
(Continued)

(58) Field of Classification Search
CPC ............ G01N 21/8806; G01N 21/956; G01N 21/898; G01N 21/8851; G01N 21/88; G01N 21/8803; G01N 21/95684; G01N 2021/3177; G01N 21/85; G01N 21/95; G01N 33/025; G01N 2021/1772; G01N 2021/1774
See application file for complete search history.

(56) References Cited

U.S. PATENT DOCUMENTS 5,449,911 A * 9/1995 Crezee ...................... B07C 5/10
250/341.7
6,610,953 B1 * 8/2003 Tao .......................... B07C 5/342
209/11

(Continued)

FOREIGN PATENT DOCUMENTS

ES 2196748 3/2001
FR 2814383 A1 3/2002
(Continued)

*Primary Examiner* — Michael P Stafira
(74) *Attorney, Agent, or Firm* — Richard M. Goldberg

(57) ABSTRACT

A method for inspecting and detecting flaws in spheroidal products involves supplying the product to a transport element formed of pairs of supporting pads, turning the product over by means of inverting the rotation of at least one of the supporting pads, lighting the product, for example, with ultraviolet light, taking images and processing these to determine whether the product is suitable or not. The machine includes transport elements made up of pairs of freely rotating supporting pads (1) placed at regular distances on a conveyor chain, elements for controlling the rotation of the supporting pads independently as these move along, lighting devices and image capturing devices, in which the rotation control items are friction guides (25,27) placed at the bottom and top which are acted on by drive tracks (11) joined to the supporting pads.

9 Claims, 4 Drawing Sheets

(51) Int. Cl.
*B07C 5/34* (2006.01)
*B07C 5/342* (2006.01)
*B65G 17/24* (2006.01)
*B65G 47/24* (2006.01)
*G01N 21/88* (2006.01)
*G01N 21/95* (2006.01)
*G01N 21/84* (2006.01)

(52) U.S. Cl.
CPC . *B07C 5/36* (2013.01); *B65G 17/24* (2013.01); *B65G 47/24* (2013.01); *G01N 21/8806* (2013.01); *G01N 21/8851* (2013.01); *G01N 21/951* (2013.01); *B07C 2501/009* (2013.01); *G01N 2021/845* (2013.01); *G01N 2021/8466* (2013.01); *G01N 2021/8854* (2013.01)

(56) References Cited

U.S. PATENT DOCUMENTS

| | | | |
|---|---|---|---|
| 6,659,287 B1 * | 12/2003 | Hawkins | B07C 5/36 |
| | | | 198/483.1 |
| 7,474,392 B2 * | 1/2009 | Van Soest | G01N 21/8806 |
| | | | 356/52 |
| 2001/0007499 A1 * | 7/2001 | Richert | G01N 21/8901 |
| | | | 356/402 |

FOREIGN PATENT DOCUMENTS

| | | |
|---|---|---|
| WO | 2009/049202 A1 | 4/2009 |
| WO | 2012/038576 A1 | 3/2012 |

* cited by examiner

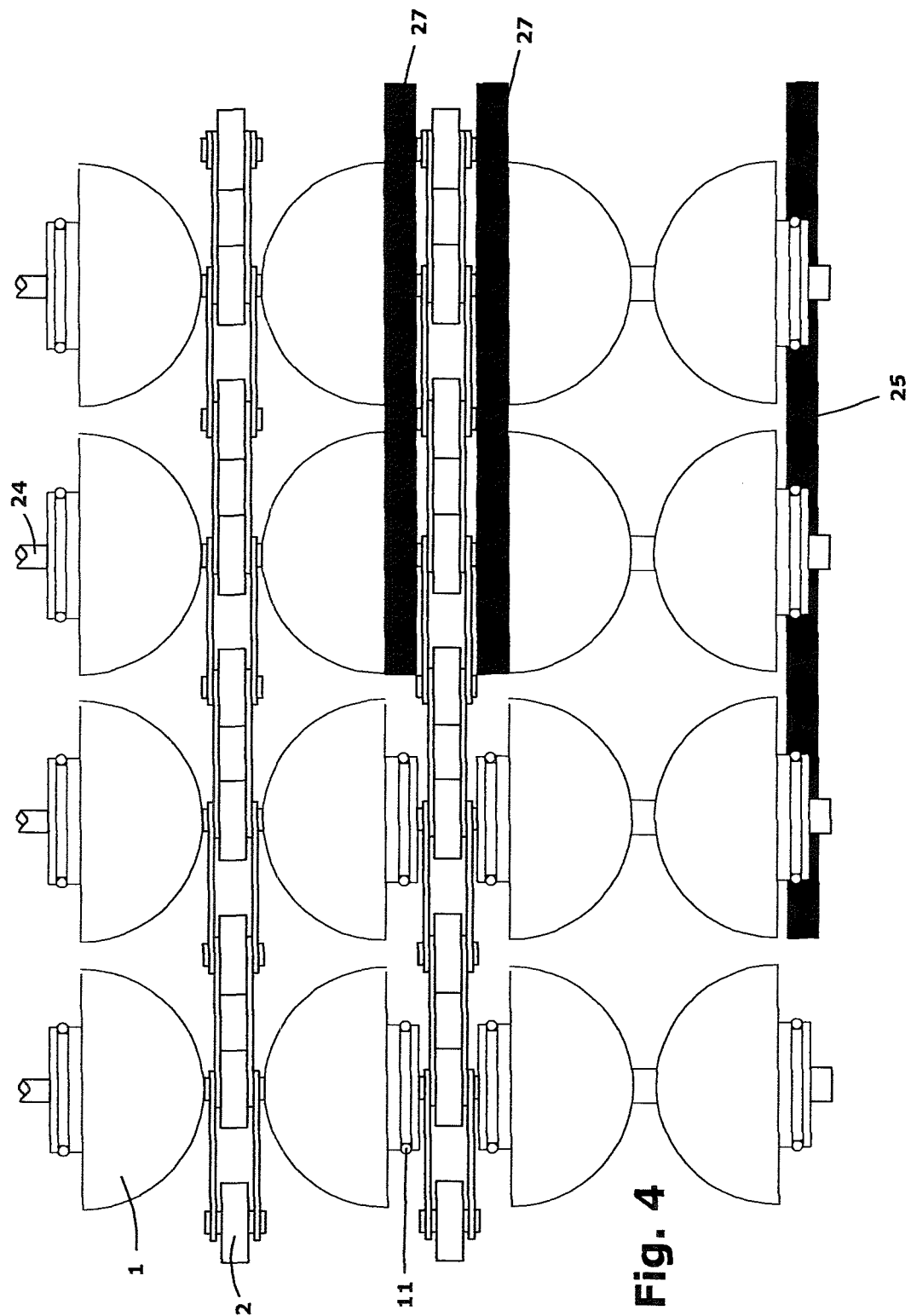

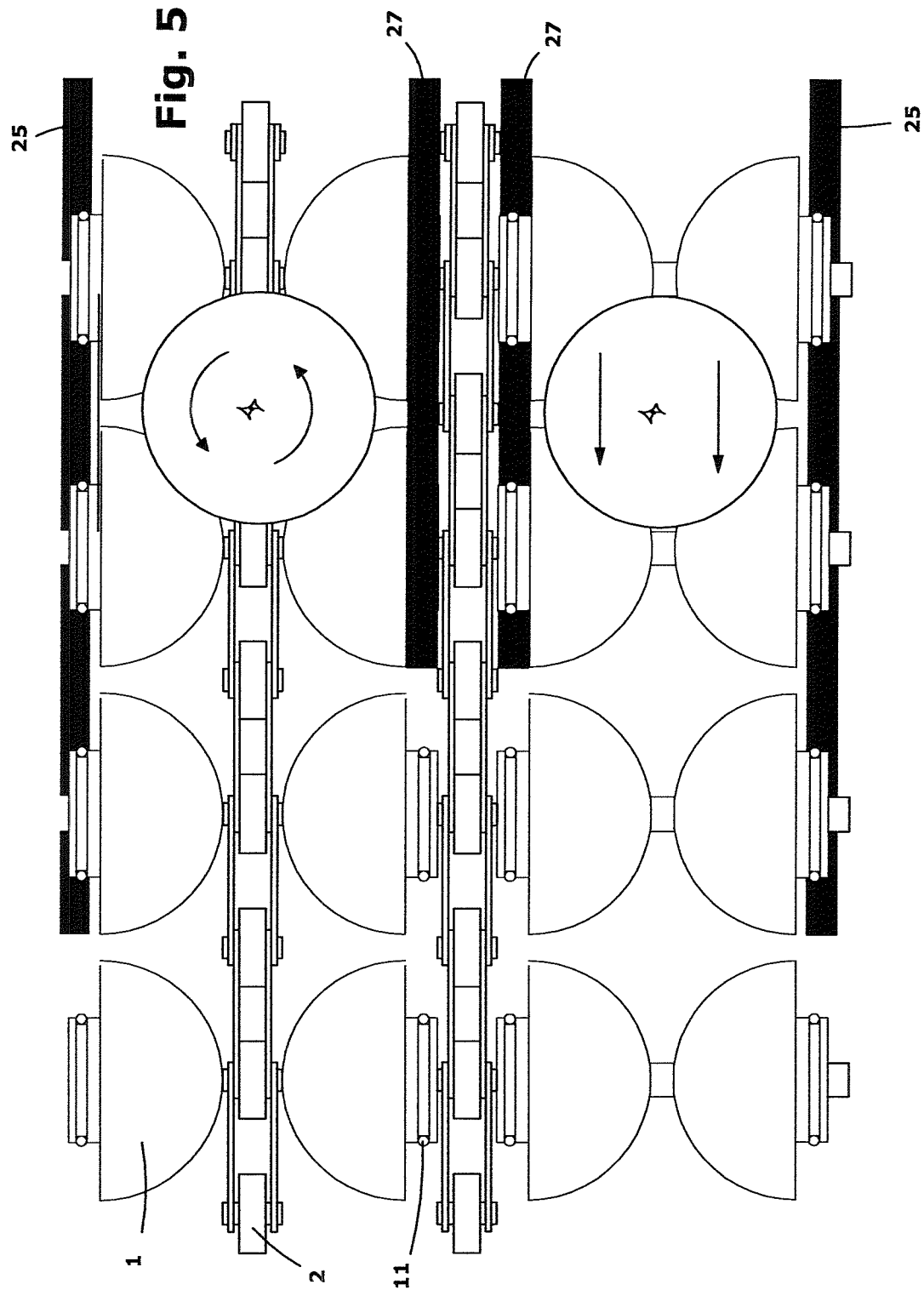

MACHINE FOR THE INSPECTION AND DETECTION OF DEFECTS IN FRUIT PRODUCTS, AND ASSOCIATED METHODS

A method for inspecting and detecting flaws in spheroidal products and a machine for implementing this method.

BACKGROUND OF THE INVENTION

This invention refers to a method for displaying spheroidal products which are carried on a conveyor chain made up of a set of pairs of supporting pads, so that each two pairs of supporting pads carry a single product: this method consists in providing a controlled rotation of the product by inverting the rotation direction of at least one of the supporting pads which carries the item along its route, so that the entire surface can be visible in a short path by means of a camera placed in an overhead position, for example. The invention also refers to a machine for implementing this method.

More specifically, the products to which the invention refers are fruit, and more specifically citrus fruit, such as oranges and mandarins.

Food products, and particularly citrus fruit, are marketed through the corresponding brands. The consumer of a brand trusts in its quality, and the marketing company needs to provide the means required for this quality to be maintained over time. One of the causes for rejecting citrus fruit is what is known as "rot", but normally due to *Phytophthora* genus fungi.

Fruit and vegetable processing plants handle a large number of the products to be treated. A processing line of a fruit and vegetable processing plant for processing and packing citrus fruit comprises several items, such as the preliminary sorting table, selectors, calibrators or sizers, conveyor belts, etc.

One of the items forming the processing lines for citrus fruit is what are known as "discotheques" in which the blemishes caused by the fungi are visible under ultraviolet light.

The action of ultraviolet light is nevertheless harmful for people and even when the selection of healthy fruit has generally been done manually up to the present time, it is desirable for the process to be carried out automatically.

There are automatic devices in which the products are made to rotate regularly, and the surface of the citrus fruit is observed by means of a set of cameras arranged on at least two side of the travel direction. This requires processing at least two sequences of images for each fruit, which proves expensive and slow.

The invention being proposed allows the entire surface area of the fruit to be displayed, and this can be observed by a single camera, in the mass-processing sequence at fruit and vegetable processing plants, so that its quality can be properly monitored for its distribution, packing and later marketing.

Hence, the purpose as a whole of this invention is to provide fruit and vegetable processing plants with an effective automatic system for eliminating rot (fruit infested by fungi which must as a priority be removed from other sound fruit in the post-harvest stage, as this affects the fruit around it by contact). It also allows the early detection of fruit with fly bites, undetectable to the human eye, and the detection of fruit that is still unripe, which enables automatic degreening in the early season, as well as other types of common defects such as blemishes, scars, branch damage, roundness and shape defects, wateriness, texture, etc.

Given that new legal norms are extremely strict as regards people's exposure to the effect of ultraviolet radiation (sorting by manual selection of rotten fruit is done at fruit and vegetable packing plants in closed areas, here commonly known as "discotheques" where blemishes are visually detected by fluorescent tubes with ultraviolet lighting.) Sorters are exposed to this ultraviolet light for the whole season, with the corresponding health and legal risks. Other automatic selection devices are extremely costly and the effectiveness of their results has not been sufficiently proven. Current regulations demand the minimum exposure and/or the suppression of these procedures.

The automatic selection system proposed is located in a selection unit to be integrated in the plant after the general sorting stage, in the place where "discotheques" are currently located and intended to replace these, before the application of waxes, but after prior selecting, washing and drying of fruit for proper visualisation with the least possible dirt.

The aim is thus to replace the current manual separation booths for separation of fruit with rot ("discotheques") located after the manual selection tables, with the system proposed, which would enable the selection and removal of fruit with common defects and rot and bites invisible to the human eye, and also possible selection and colour discrimination, which would allow degreening in the early season. This represents an extraordinary improvement for installations with mechanical calibration, as this can easily be adapted, without having to make large investments in reintroduction of this machinery.

STATE OF THE ART

At the present time there are fruit transport systems for its discrimination and later size-grading integrated as components of electronic calibration systems able to differentiate fruit and examine its surface, in order to evaluate this according to quality parameters by optical selection of defects. Later on its equatorial diameter, its weight and volume are gauged and this is distributed by belts integrated in the sizer which distribute the fruit calibrated in this way to different zones for preparing and packing the product.

Although such installations have meant a great step forward in the information on the fruit to be processed and its computer processing, they require a great financial investment as well as a large surface area to be installed and integrated in the set of machinery at a fruit and vegetable packing plant.

The installation of an electronic calibration system requires linear distribution of its structure and distribution belts perpendicular to this, distributed over its whole length at minimum distances from each other, which entails major demands as regards the size of machinery and thus great expense and long payback periods as compared with conventional central calibration with tilting rollers.

In electronic calibration of the fruit and vegetable products mentioned above, systems for transporting and differentiating fruit for its calibration and later distribution are used with similar technical solutions in the majority of calibration systems currently found on the market.

The system used consists of a group of prior belts known as singulators, forming a group of parallel tracks, these belts being arranged in groups of two, forming a V shape, at an angle of roughly 90°. The fruit coming from the processing line is carried along these singulating belts one by one. The size of this first assembly depends on the production and manufacturer's requirements, usually being about five meters long.

After the singulator belts mentioned, there is a following module known as differentiator which is synchronised with the singulator belts. This is a set of chains which support bobbin rollers (or diabolos) on the sides, mounted on respective axles in sets of two along their entire length. Between each set of two bobbin rollers there is a system for extracting products by a tab with a spring or similar which removes the product laterally in the gap between two chains made for this purpose.

These bobbin rollers make the fruit rotate on itself. The fruit then turns, supported on its equatorial diameter, enabling this to be viewed and scanned for later quality assessment. However, since the fruit turns on a horizontal axis, it is difficult to evaluate this with a single camera, and even with two cameras per track a differentiated view of the product is not obtained with the minimum space allowed for artificial vision. This whole set of systems requires a large amount of space for its set-up and a large surface area for distribution of the processed fruit, apart from replacing the usual calibration installations with tilting rollers. These rollers work properly but do not give individualised information on the product, for which reason it is not possible to degreen this in the early season stage nor to automatically separate any fruit with rot. At the same time, evaluation in quality parameters, the priority for investment in this type of machinery, still fails to give the results achieved by manual evaluation. For this reason enormous investments in electronic calibration systems are difficult to pay off as they need manual supervision (known as re-sorting) before allowing the product into preparation zones (for distribution or boxing).

FR 2814383 describes a Device for sorting products, particularly fruit, which comprises a conveyor belt provided with pairs of diabolo rollers in which each two of these houses one of the pieces of fruit carried; to make these rotate the rollers are driven along their travel by withdrawable ramps. It has nevertheless been shown that rotation by means of friction of the guides in the rotation direction does not give satisfactory results, because the rotation is incomplete or does not take place.

SUMMARY OF THE INVENTION

The aim of the invention is thus a method to make the fruit rotate in a spiral, gradually modifying the position of its rotation axis, by inverting the movement of at least one of the fruit supporting pads for its quality diagnosis and differentiation by means of artificial vision and later continuous distribution. The inverted movement, in the opposite direction to that of its rolling on a lower support, is preferably activated by means of friction guides arranged at the top of the supporting pads.

This also describes a machine integrating a fruit conveyor system in the form of a set of conveyor chains with synchronised movement. Although for simplicity's sake this describes a single line, the scope of the invention similarly covers a set of lines arranged in parallel, provided with a single drive system for all of these or with separate drive means for each one and with a single camera for imaging, or with different cameras for each one. The construction of multiple units could be modular, having these joined by simple juxtaposition, or made up of units of several elements. The chains drag the axles along at regular distances; each axle carries at least two supporting pads (a single axle can be common to several lines, in which case it will have as many pairs of supporting pads as the machine has lines) preferably in a hemispherical shape, with curves facing each other. Each two pairs of successive supporting pads on a line, each pair being supported by the relevant axle, constitutes a housing or cradle for one piece of fruit. In the movement of the chains, each axle and its corresponding supporting pads are moved along the machine travel, in an upper position, and returned in a lower position. The supporting pads are concentric to the carrying axles and there is no restriction of their rotation relative to each other, meaning that the supporting pad rotation is free. The invention being proposed thus consists of an automatic identifier for later selection of the fruit, which is made up of a set of tracks comprising two or more chains pulling along hemispheres made of rubber or some similar foodstuff-quality material, which hold the fruit by direct contact and which we will hereinafter call "supporting pads". The supporting pads are mounted on the modular chains facing each other, so that each pair of these and the following or previous pair form a housing which cradles each piece of fruit, holding this by four support points, and which conveys a movement to the fruit from each of said support points in accordance with the movement of said supporting pads. These support points on each of the supporting pads are the items used by the system to control the fruit's position and rotation.

Along the travel there are a number of drive tracks, some set at the top of the supporting pads and others at the bottom, so that these tracks independently induce each of the supporting pads to move in one direction, in the opposite one, or if they had no contact with any track, rotating in accordance with the movement provided by the fruit.

Hence, in accordance with the combination of rotation directions, the fruit can be made to move as required, so that its entire surface is displayed in a particular direction, normally in a vertical direction, where the detector camera is located. The orientation of the fruit alters along the track, displaying its entire surface in all directions by selective rotation, doing this in the minimum space and time.

It should be pointed out that when a spherical or geoid-shaped fruit is located and carried on a support chain like the one described, it tends to balance its inertia mass distribution in its rotation movement and take up its balance position rotating on its natural axis with the petiole at one end and the flower at the other. This hinders overhead observation of the fruit during its stable transit in the observation section because the sides of the fruit cannot accurately be seen and it no longer changes that position along its whole travel. It is thus vital to be able to have a system like the one described to modify its position at will during its transport under the observation system.

The supporting pads or hemispheres, which can turn freely in respect of their axle, roll in their forward movement at different speeds and/or with different rotation directions, through the action of friction guides located at the top and bottom of these, so that it is the pad resting against the lower guides which gives the supporting pads their forward movement, and the pad resting against the upper guides which determines the movement opposite to forward direction. The different speed or direction of the movement of the different supports gives the fruit a variable movement depending on the way the supporting pads rest on said friction guides.

For modifying the rotation speed of the supporting pads, these have external drive tracks against the friction guides joined to them. Different rotation speeds or directions are obtained depending on the position of the guides and the diameter of the guides, so that this enables giving the fruit the required controlled rotation movement in respect of the horizontal axis (when all the supporting pads are rotating in the same direction), and with a vertical component (when one or more supporting pads rotate the opposite way to the others). Along its travel the fruit thus displays its entire surface towards the artificial vision system located overhead on the chain for its scanning in transit in the minimum possible space in order to reduce the size of the assembly.

The speed and rotation of the fruit in its travel on the chain thus depends on the rotation speed of the supporting pads on which this rests, and said rotation speed of the supporting pads takes place through the contact with guide tracks normally located on the outside of said supporting pads on the friction guides located on the bedframe of the assembly.

As a result of this movement, and given that the fruit is moved through its support points, the fruit displays its upper surface, all along its transit through the machine. This facilitates its inspection from a single viewpoint at which an image-capturing camera will be placed, normally in an overhead position, but this observation can obviously be from other or more angles.

The friction guides are located on an upper or lower plane to the supporting pads. In their movement the supporting pads will come into contract with said friction guides; insofar as there is longitudinal displacement of the supporting pads through the movement of the chains supporting their axles, contact with the friction guides will cause tangential support, which will make the corresponding supporting pad rotate. Said friction guides are longitudinally mounted at the bottom or top of the chain. When the friction guides are located at the bottom, the supporting pads will rotate in a particular direction, while if the friction guides are located at the top the direction will be the opposite one. Depending on the diameter of the drive tracks a particular rotation speed will be obtained. The supporting pads touching friction guides in drive tracks with a greater diameter will rotate at a slower speed than the ones which do so with smaller-diameter drive tracks, taking into account that the travel speed is the same for all of these. In their displacement the drive tracks of the supporting pads can come into contact with a lower friction guide, with an upper friction guide, or with neither of these, forcing a rotation movement in one direction, in the opposite one, or according to the rotation induced by the fruit (due to the movement transferred by the other supporting pads), when the supporting pad does not come into contact with any friction guide. This creates movements in the support housing which drag the fruit located on these and make it roll through the effect of the force exerted at a speed which depends on the diameter of the supporting pads in the contact position. When a supporting pad rests its dragging track on an upper friction guide and the others do so on lower tracks in one section of the travel, this supporting pad will rotate in the opposite direction and instantaneously make the fruit rotate in respect of a vertical axis. Depending on the length of the friction guide the rotation angle which will turn the fruit in respect of the vertical axis can be controlled.

When any of the supporting pads rubs against a lower guide section during the transit of the chain this supporting pad will rotate in a first direction (its upper surface rotates in the direction of the chain's forward movement); when it ceases to rub against the lower guide and rubs against an upper guide, its rotation is inverted (its upper surface rotates in the opposite direction to the chain advance) which gives the fruit a rotation in respect of a vertical axis or with a vertical component during that part of its travel. When it comes up against a lower guide again, the initially described rotation is restored, but having made the fruit rotate, for example, at 90°, for which reason the parts of the fruit concealed in the previous display prior to the change in direction will be shown over the new rotation.

The intention is thus to discriminate the healthy fruit from the fruit with faults, so that the following phase comprises separating one sort from the other at different points in accordance with the classification that the computer system has determined, whether the fruit is healthy or not.

Since the supporting pads are freely rotating, the supporting pad on one of the sides can turn in one direction and its corresponding partner the other way, or both in the same direction but at a different speed, depending on how these rest on the friction guides.

The rotation of the supporting pads causes a modification to the rotation axis of the fruit housed in this. As there are forces of different intensity (different rotations and speeds, or inverse rotations) the fruit goes on turning according to a horizontal axis, which is different in absolute terms referring to the initial rotation of the fruit). Hence, in a first phase the fruit displays practically all its surface area upwards through a 360° rotation; after the rotation of the fruit caused by the different speeds of the supporting pads, the points of the fruit located in the geometrical rotation axis go into another position, for which reason, by going on turning, the previously concealed points (at the ends of the rotation axis) are now effectively displayed (as they have been moved from the ends of the rotation axis) upwards, and the images obtained by a camera located above or by a set of cameras can be analysed.

This invention thus describes a system which enables controlling the mechanical pulls on the surface of the fruit so that this rotates on itself and makes its geometrical axis position change, to ensure rotation in respect of the new rotation axis after the position has changed, so that the fruit gradually presents all its surface area during its transit in the minimum space towards a certain direction, for example, an overhead position.

To sum up, the solution being proposed determines a forced change in the rotation direction of some supporting pads in respect of others for a short specific time, so that this exerts a torque force on the fruit which changes the rotation axis around which it was turning and makes it rotate on itself and go on to exhibit its sides.

This objective is achieved by brushing at least one of the supporting pads from one of the sides with a friction guide set at the top of the drive track for the relevant supporting pad, and keeping the rest under the friction of the lower guides. This makes the instantaneous horizontal rotation of the fruit, overcoming the gyroscopic force that the fruit had and describing a spiral until recovering its initial position. This is the solution used to force its complete display for quality diagnosis.

The friction guides placed in appropriate positions on the frame, in combination with the drive tracks of the supporting pads, form the mechanisms rotating said supporting pads to make the fruit rotate at the required time to ensure proper display during its transit.

The system proposed enables causing more than one change in direction of the fruit by using more than one friction guide along the travel.

As was stated above, the invention assembly is modular, meaning that an unlimited number of units like the one described can be set in parallel and can share certain items or not, such as for example motors or drag chains.

Throughout the display, at least one camera placed in an overhead position obtains images of the surface displayed of the fruit. For proper processing, the fruit is subjected to a suitable light source and the images obtained are computer-processed to determine whether the fruit is accepted or rejected, or even the degree of rejection (total, for juice, . . . ).

BRIEF DESCRIPTION OF THE DRAWINGS

In order to illustrate the explanation of the invention now being described, we are enclosing four sheets of drawings with this descriptive report, in which five figures represent the essence of this invention as an example, without constituting any limitation thereto, and in which:

FIG. 4 shows an upper view of one part of a set of two lines of modular chains joined together;

FIG. 5 shows a view like FIG. 4, in which the fruit is being rotated driven by the supporting pads; this comprises an additional friction guide as compared with FIG. 4; on one of the lines there is one upper friction guide and one lower one, causing the rotation (the change in the rotation axis) in the other two lower friction guides, causing dragging (rotation) without changing the rotation axis;

Figure 1:
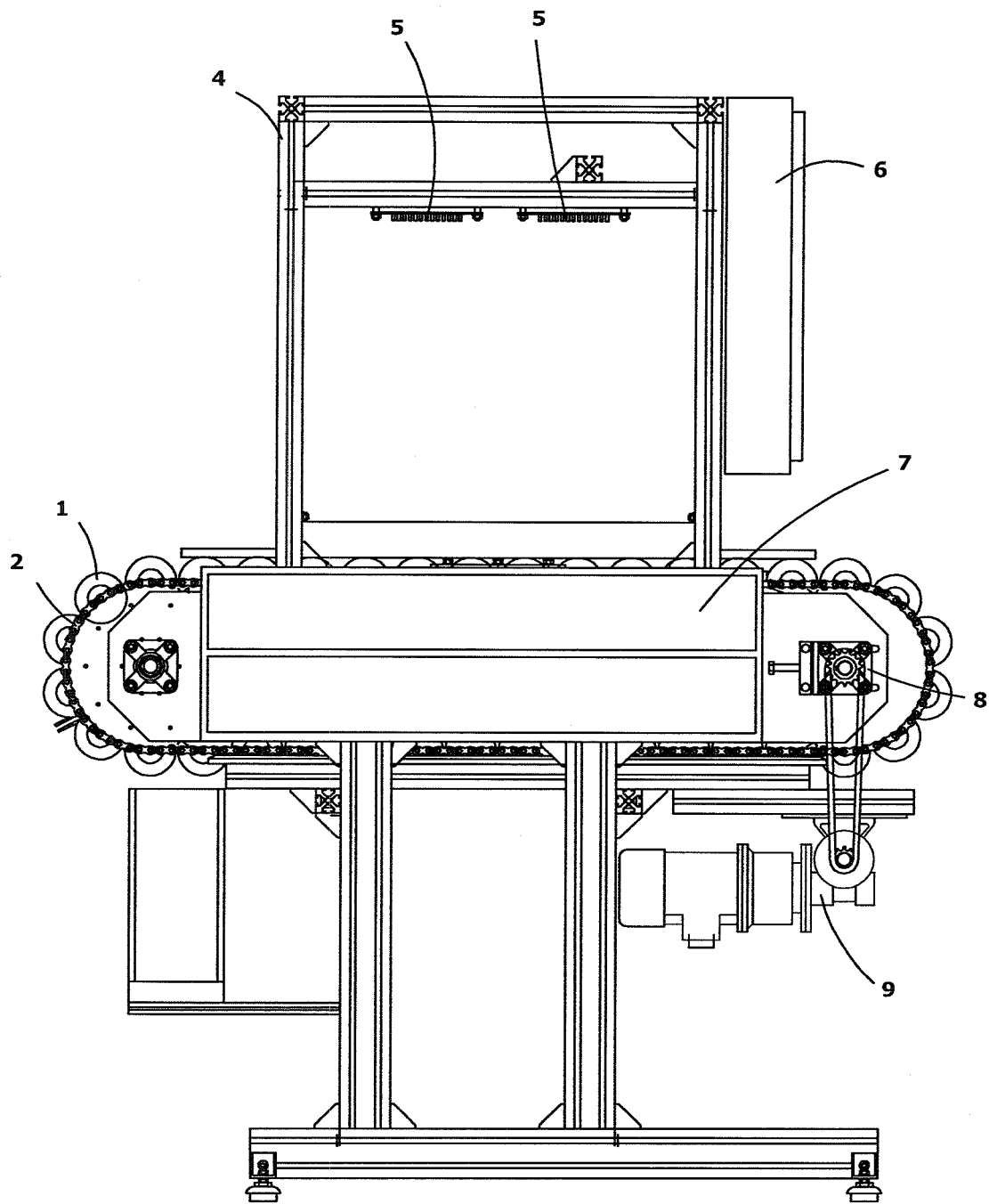
FIG. 1 shows a side view of the machine of the invention.
Figure 2:
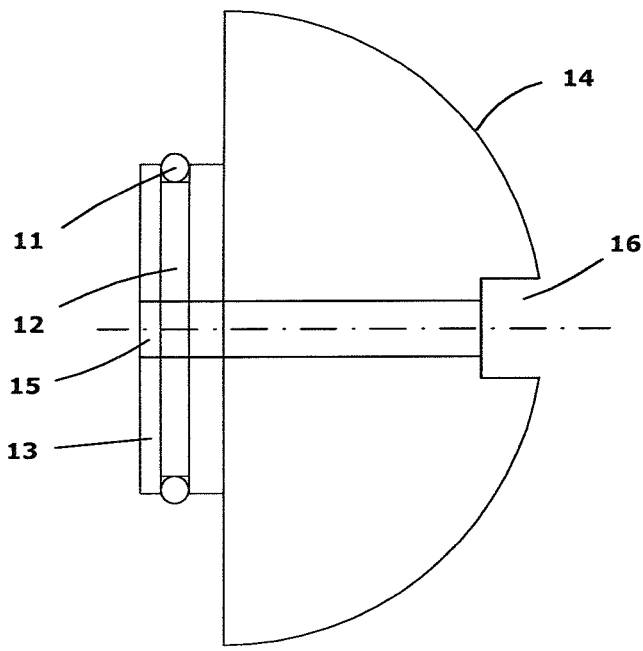
FIG. 2 represents a front view of a supporting pad.
Figure 3:
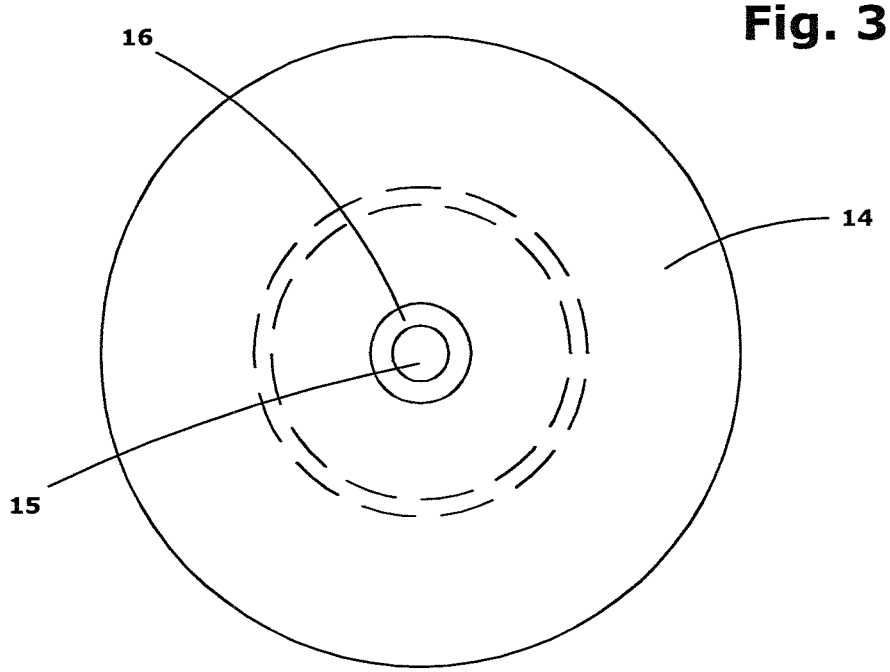
FIG. 3 shows a side view of the supporting pad of FIG. 2.

The following references are used in these figures:
1 Supporting pads
2 Conveyor chain
4 Upper frame; this is modular and surrounds the systems for lighting and artificial vision
Lighting device: the light will be as required for scanning (ultraviolet, white, infrared light, etc.)
6 Electric and electronic control panel
7 Main frame: this is modular, and is normally made of aluminium, steel or some other material for supporting bodies and adapted for its lateral extension
8 Drive/take up head for the drag chains
9 Motor—electronic drive
11 Drive track; this item is for brushing by the friction guides, by an "O" ring integrated in a seat formed of a lateral recess of the supporting pads or by covering the assembly with rubber.
12 "Seat for the "O" ring.
13 Side recess; smaller in diameter than the supporting pad, to enable increasing the rotation speed by resting on the friction guides
14 Main body of the supporting pad; this has a hemispherical profile which can be made eccentric depending on the type and morphology of the fruit to be processed
15 Hole for the drive axles
16 Seat for the spacers of the opposite supporting pad
25 Lower friction guide
27 Upper friction guide

PREFERENTIAL EMBODIMENT OF THE INVENTION

The purpose of this invention is a method for inspecting and detecting flaws in spheroidal products, particularly fruit, which comprises:

Supplying to a transport element, this transport element being formed of a set of supporting pads arranged in pairs, each two pairs constituting a housing for a single product, and whose displacement is synchronised;

Turning over to modify the rotation axis during displacement, so the entire surface area is displayed in a certain direction, for example an overhead position: the overturning is done by inverting the rotation movement of at least one of the supporting pads in respect of the others on which the fruit is resting, along part of the displacement travel of said supporting pads; the normal movement of the supporting pads is provided by the support of a drive track joined to each supporting pad on a corresponding friction guide set at the bottom of the rotation axis of said supporting pad; the inverse movement is done by resting the drive track of the corresponding supporting pad on a friction guide placed at the top of the rotation axis of the supporting pad;

The lighting of the product along the display travel; the lighting will be of the right wavelength to stress the type of flaw whose determination is being sought; in the case of citrus fruit, and for detection of fungi, generating fruit rot, ultraviolet light will be used;

Imaging along the display travel covering the entirety of the product: and

Processing the images by computer to determine whether the product is appropriate or not, depending on the analysis of the images for its later selection and separation.

The invention also extends to a machine which enables the performance of this method, for diagnosis of the condition of a large number of products, and in particular of fresh spheroidal fruit, and for handling this with great accuracy, speed and efficiency, as part of an installation for processing fruit and vegetables, in which any stoppage through breakdowns or reduction of performance causes enormous damages.

The machine is made on a solid, compact frame which surrounds and holds the different parts of the system. This obviously has to adapt to the fruit input and output heights required by the installation. For height adjustment of the items the frame is designed to incorporate legs with adjustable height supports.

According to one embodiment, the frame is made of assembled structural aluminium profiles to hold the items, or made of stainless steel plate for protecting this from the industrial environment in which this is located.

The machine of the invention is modular, meaning that the installation can "grow" or adapt to installations of any size by adding modules in parallel, being able to share some common items, such as control systems or drive items.

A two-line module is described as an example of the embodiment, as this is considered to be the most appropriate for later expansion. The machine thus houses two lines of modular chains comprising the following items:

Systems for rotating and controlling the display of fruit
Artificial vision systems
Integrated control panel As seen in FIG. 1, the machine is made up of a main frame (7), which holds two heads, one a drive/take-up head (8) with its motor (9) located at one end of the machine, and another frontal freely-rotating head located at the other end of the machine, where there is a retention mechanism for discriminated fruit. The two heads comprise pinions or sets of pinions which pull two drag chains (2). These chains (2) are made up of elements, and every certain number of elements the corresponding element holds an axle rotating freely in respect of the element of said chain. The axle can be held at more than one point by more than one element of a chain (2). According to a preferential embodiment, the chain is made up of elements of roughly % inch. The axles held by the chains house pairs of supporting pads (1), at regular distances. According to the two-line embodiment described, each axle will house two parts of supporting pads and will be pulled by one or more chains. Each line could nevertheless have independent axles from those of the other line. According to one embodiment, the axles carrying the supporting pads (1) are pulled by three chains. The supporting pads (1) are made up of hemispheres or truncated cones with variable profile, converging towards the centre of the pair which these form; each two pairs of successive supporting pads (1) form a housing for one piece of fruit. The supporting pads are for example made of rubber, or any other foodstuff-quality, rough material; their sizes will be as appropriate for the fruit to be treated, and they will be arranged at regular intervals, for example, every two elements of the chain. At least the top of the chain travel is protected by a chain cover, which prevents contact with the fruit and facilitates its maintenance.

Over the main frame there is an upper frame (4), which houses the lighting systems (5) and cameras for capturing images, as well as holding the control panel (6).

The supporting pads (1) are mounted on the axles in such a way that there are spacers between each pair of these, and for securing the ends of the axles these are provided with a slot for securing by circlips.

The supporting pads have a main body (14) whose surface has a hemisphere or truncated conical shape with variable profile, and have a hole (15) which goes through the carrying axle. They have a side recess (13) which forms a recess or seat (12) for a joint which forms a drive track (11). The greater or lesser diameter of the side recess (13) will determine the corresponding rotation speed when this rests on the relevant friction guides. The zone with smaller diameter has a recess which forms a seat (16) for spacer elements in respect of the opposite supporting pad.

Along the travel of the supporting pads, and set in the main frame, there are longitudinal friction guides (25, 27), which could be arranged in an upper (27) or lower (25) position. The friction guides are for brushing and consequently turning the supporting pads, and freely rotating in respect of their axle. If these are brushed by an upper friction guide (27), the rotation direction will be opposite to that of a lower friction guide (25).

According to a non-preferred option, each supporting pad of the four forming the fruit cradle is driven by a different friction guide, the drive tracks joined to the supporting pads being displaced to different distances from these supporting pads to this end.

FIG. 4 shows the way different lateral guides have been fitted on one of the selection lines, a lower one (25) on the right-hand side (in the direction of travel) and an upper one (27) on its left-hand side. The supporting pads from one line rotate in the opposite direction to the ones opposite, which makes the fruit twist about its equatorial diameter, making it rotate on itself, thus physically modifying its director rotation axis which is commanded by its inertia force during its transport and rotation. On one of the lines in FIG. 5 line two friction guides (25) have been applied at the bottom of the supporting pads, which makes the fruit rotate in a longitudinal direction opposite to the pulling direction of the supporting pads.

Hence, in keeping with the position and length of the friction guides and of the diameters of the recesses (13) of the supporting pads which hold the joint which constitutes the drive track (11), this determines the rotation speed and direction of the supporting pads, and thereby total control of the fruit that they hold.

The assembly has a system for detecting the condition of the fruit, in order to determine whether this continues along the processing line or is removed from this. The system comprises a lighting device (5), and at least one detection camera, which determines whether the fruit is suitable or has to be rejected, by means of an information-processing system.

What is claimed is:

1. An automatic machine for inspecting and detecting flaws in spheroidal fresh fruit, as to quality evaluation for rot and external flaws, that can be integrated in a processing line of plants for the fruit, comprising:
    transport elements for the fruit which include a set of pairs of supporting pads, mounted on parallel axles which allow free and independent rotation of each supporting pad, in which each two pairs of supporting pads determine a housing for a product to be transported;
    at least one conveyor chain for the axles carrying the supporting pads, in which the supporting pads take up fixed positions at regular distances on the conveyor chain;
    a lighting device for the products along a display route therefor;
    a device for capturing images of the surface of the product; and
    a set of control items which determine rotation speed and direction of each of said supporting pads, and consequently movement of the products on the transport elements, the control items including drive tracks on the supporting pads, and longitudinally mounted friction guides on the frame with which each supporting pad is given a required movement, and the friction guides are placed in lower and upper positions in respect of the axles of the supporting pads, such that each fruit is guided at any given time by two pairs of said supporting pads, with said set of control items adapted to rotate at least one of said pads of at least one pair at least at one of:
        different speeds, and
        different directions
    relative to another said pad in order to impart a rotation to the fruit in a direction at an angle to the direction of travel of the fruit such that the entire surface of the fruit is adapted to be viewed by said device for capturing images.

2. An automatic machine for inspecting, detecting and separating fresh fruit in its quality evaluation for rot and external flaws, according to claim 1, wherein the supporting pads are in one of hemispherical and truncated conical shape with variable sections.

3. An automatic machine for inspecting, detecting and separating fresh fruit in its quality evaluation for rot and external flaws, according to claim 2, wherein hemispheres thereof are made of a rough, foodstuff-quality material.

4. An automatic machine for inspecting, detecting and separating fresh fruit in its quality evaluation for rot and external flaws, according to claim 1, further comprising:
    an artificial vision system, provided with light emitters in different wavelengths, which scans the fruit in movement by overhead observation and determines whether the fruit has to be accepted or rejected, and
    a device for identifying the position of the fruit examined.

5. A method for inspecting and detecting flaws in spheroidal fruit, comprising the steps of:
    supplying the fruit to a transport element, said transport element being formed of a set of supporting pads arranged in pairs, every two pairs constituting a housing for a single product, and displacement of the supporting pads being synchronised;
    rotating at least one of said pads of at least one pair at least at one of:
        different speeds, and
        different directions relative to another said pad in order to impart a rotation to the fruit in a direction at an angle to the direction of travel of the fruit so that an entire surface area of the fruit is displayed in a certain direction;
    lighting of the fruit along the display travel with a wavelength to bring out a type of flaw whose determination is being attempted to be viewed;
    imaging along the display travel covering the entirety of the fruit; and processing images obtained by said imaging by computer methods to determine whether the fruit is appropriate or not, depending on analysis of the images, for its later selection and separation.

6. A method for inspecting and detecting flaws in spheroidal fruit, according to claim 5, wherein movement of the supporting pads is provided by support of a drive track joined to each supporting pad on a corresponding friction guide.

7. A method for inspecting and detecting flaws in spheroidal fruit, according to claim 6, wherein movement of the supporting pads in one rotation direction is determined by a drive track joined to each supporting pad resting on a friction guide placed at a bottom of the rotation axis of the supporting pad and in that the movement of the supporting pads in an opposite rotation direction is performed by a drive track of the corresponding supporting pad resting on a friction guide placed at a top of the rotation axis of the supporting pad.

8. An automatic machine for inspecting, detecting and separating fresh fruit in its quality evaluation for rot and external flaws, according to claim 1, wherein the rough, foodstuff-quality material is rubber.

9. A method for inspecting and detecting flaws in spheroidal fruit, according to claim 5, wherein in the case of citrus fruit, and for detection of fungi, generating fruit rot, ultraviolet light is used.

* * * * *